(12) United States Patent
Wahler et al.

(10) Patent No.: US 9,901,275 B2
(45) Date of Patent: Feb. 27, 2018

(54) OVERVOLTAGE PROTECTION FOR DEFIBRILLATOR

(75) Inventors: Bruce Andrew Wahler, Ashby, MA (US); David K. Hunt, Nashua, NH (US); Aziz L'Bahy, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 13/509,450

(22) PCT Filed: Nov. 10, 2010

(86) PCT No.: PCT/IB2010/055109
§ 371 (c)(1),
(2), (4) Date: Sep. 14, 2012

(87) PCT Pub. No.: WO2011/058506
PCT Pub. Date: May 19, 2011

(65) Prior Publication Data
US 2013/0131526 A1    May 23, 2013

Related U.S. Application Data

(60) Provisional application No. 61/261,389, filed on Nov. 16, 2009.

(51) Int. Cl.
*A61B 5/0424*    (2006.01)
*H02H 9/04*    (2006.01)
*A61N 1/39*    (2006.01)

(52) U.S. Cl.
CPC .......... *A61B 5/0424* (2013.01); *A61N 1/3931* (2013.01); *H02H 9/045* (2013.01)

(58) Field of Classification Search
CPC .. H03K 19/00346; H03K 17/08; H03K 17/16; H01L 27/0248; H01L 27/0255; H01L 27/0288; H02H 9/04; H02H 9/046; H02H 9/06; H02H 9/045; H01T 4/00; H01T 2/00; A61B 5/0424; A61N 1/3931
(Continued)

(56) References Cited

U.S. PATENT DOCUMENTS 2,290,526 A * 7/1942 Slepian et al. ................ 313/608
2,922,914 A * 1/1960 Carpenter et al. ............ 313/308
(Continued)

FOREIGN PATENT DOCUMENTS

DE    2445141 A1    9/1974
DE    2832470 A1    7/1978
(Continued)

*Primary Examiner* — Mark W Bockelman
*Assistant Examiner* — Jeremiah Kimball

(57) ABSTRACT

A defibrillation circuit comprising a gas discharge tube and a light source arranged to pre-energize the gas discharge tube in order to provide predictable breakdown conditions of the gas discharge tube. The gas discharge tube may be used as an overvoltage protection device for the defibrillation circuit or for certain parts of the defibrillation circuit. An overvoltage protection device for medical devices is also described. The overvoltage protection device comprises a gas discharge tube and a light source arranged to pre-energize the gas discharge tube in order to provide predictable breakdown conditions of the gas discharge tube.

6 Claims, 2 Drawing Sheets

(58) Field of Classification Search
USPC .............................. 607/5; 361/120, 56, 91.1
See application file for complete search history.

(56) References Cited

U.S. PATENT DOCUMENTS

| | | | | |
|---|---|---|---|---|
| 3,162,741 | A * | 12/1964 | Lindgren | 337/25 |
| 3,223,874 | A * | 12/1965 | Carpenter | 313/231.11 |
| 3,242,376 | A * | 3/1966 | Schultz | 315/36 |
| 3,377,503 | A * | 4/1968 | Osterhout | 315/36 |
| 3,496,409 | A * | 2/1970 | Connell | 315/36 |
| 3,653,387 | A * | 4/1972 | Ceier | 600/525 |
| 4,123,682 | A * | 10/1978 | Lange et al. | 313/54 |
| 4,707,762 | A * | 11/1987 | Yapoujian | 361/124 |
| 5,285,779 | A | 2/1994 | Cameron et al. | |
| 6,686,876 | B1 * | 2/2004 | Patel | 342/198 |
| 7,053,536 | B1 | 5/2006 | Boman et al. | |
| 2004/0256975 | A1 | 12/2004 | Gao et al. | |
| 2006/0155354 | A1 * | 7/2006 | Heath | 607/142 |
| 2007/0297782 | A1 | 12/2007 | Kleverman et al. | |
| 2009/0210022 | A1 * | 8/2009 | Powers | 607/5 |

FOREIGN PATENT DOCUMENTS

| | | | |
|---|---|---|---|
| DE | 2832470 | C2 | 7/1978 |
| JP | H067461 | A | 1/1994 |
| JP | 2001297853 | A | 10/2001 |
| WO | 9850990 | A1 | 11/1998 |

* cited by examiner

OVERVOLTAGE PROTECTION FOR DEFIBRILLATOR

FIELD OF THE INVENTION

The field of the present invention relates to a defibrillation circuit, and in particular to overvoltage protection within the defibrillation circuit. The field of the present invention also relates to an overvoltage protection device for medical devices.

BACKGROUND OF THE INVENTION

Defibrillators deliver a high-voltage pulse to the heart in order to restore normal rhythm and contractile function in patients who are experiencing arrhythmia, such as ventricular fibrillation ("VF") or ventricular tachycardia ("VT") that is not accompanied by a palpable pulse. There are several classes of defibrillators, including manual defibrillators, implantable defibrillators, and automatic external defibrillators (AEDs). AEDs differ from manual defibrillators in that AEDs are pre-programmed to automatically analyze an electrocardiogram (ECG) rhythm to determine if defibrillation is necessary and to provide administration measures such as shock sequences and cardio pulmonary resuscitation (CPR) periods. To this end AEDs, but possibly also other types of defibrillator, comprise an ECG monitoring circuitry. Some types of defibrillators use the ECG monitoring circuitry to provide a 'demand pacing' function, wherein the ECG monitoring circuitry continually compares the patient's heartbeat to a desired outcome, and provides additional stimulus if the heart cannot maintain its required performance.

ECG signals are relatively weak electrical signals. The ECG monitoring circuitry needs to be sensitive enough to detect and analyze the ECG signals. The defibrillator also comprises high-voltage circuitry for generating a high-voltage pulse to be administered to the patient. The high-voltage pulse is conducted via a set of defibrillation leads to a set of defibrillation pads which are attached to the patient. Depending on the design of the defibrillator, the high-voltage circuitry and the ECG monitoring circuitry share the same pads and leads, or the ECG monitoring circuitry is connected to the patient via dedicated monitoring leads and monitoring pads.

When a high-voltage pulse is administered to the patient by means of the high-voltage circuitry, the high-voltage pulse is also transmitted to the ECG monitoring circuitry. The ECG monitoring circuitry receives substantially the full high-voltage pulse if the ECG monitoring circuitry shares the defibrillation pads and/or defibrillation leads with the high-voltage circuitry. Even if the ECG monitoring circuitry uses separate monitoring pads and monitoring leads, a significant portion of the high-voltage pulse may reach the ECG monitoring circuitry due to electrical coupling through the body of the patient. Therefore, it is usually necessary to protect the ECG monitoring circuitry in a defibrillator.

Protecting an ECG monitoring circuitry in a defibrillator is a challenging design problem. The monitoring circuitry has very high impendence and detection of improper patient connection requires detecting small changes in operating current, usually on the order of a few nanoamperes. At the same time, the monitoring circuitry will be exposed to brief high-voltage transients many times over the life of the defibrillator. Many overvoltage protection devices that work well in other applications require far too much steady-state power to be applied to such a circuit. Gas discharge tubes (GDTs), or spark gap devices, are a notable exception: they combine the attributes of moderate clamping voltages, very high impedance in their uncharged state, and fast operation. For these reasons, GDTs are the protection device of choice in ECG monitoring circuitry for modern defibrillators.

The inventors of the teachings disclosed herein have realized that gas discharge tubes (GDTs) may exhibit an unpredictable behavior with respect to their breakdown voltage and the time it takes for them to change between a high-impedance mode to a short-circuit mode. GDTs require a certain level of steady-state gas ionization activity. Without this ionization, the GDT may remain in its linear operating mode during a high-voltage pulse. The GDT may even remain in the off state for a portion of the high-voltage pulse. While in its linear operating mode the GDT only conducts a relatively small current. This means that a device to be protected by the GDT would be exposed to the high-voltage pulse for quite some time, or that a significant amount of electrical current would be discharged via the device to be protected, for example the ECG monitoring circuitry. The GDT may also take a comparatively long time (several milliseconds) to change state when first excited, risking damage to the circuit that the GDT protects.

A traditional method of promoting a prompt arc-over is to add a small amount of radioactive material to the ionizing gas in the GDT. This method is no longer desirable due to environmental and health reasons.

SUMMARY OF THE INVENTION

It would be desirable to provide a defibrillation circuit in which reliable overvoltage protection is achieved by means of GDTs, but without using radioactive material to pre-ionize the gas. This desire and/or possible other desires are addressed by a defibrillation circuit comprising a gas discharge tube and a light source arranged to pre-energize the gas discharge tube in order to provide predictable breakdown conditions of the gas discharge tube. The light source may pre-energize the gas discharge tube either by ionizing the gas or by means of a photoelectric effect on the anode and/or cathode of the gas discharge tube, which ionizes the gas indirectly. The amount of light output from the light source can be calculated or estimated in advance so that the amount of ionized gas can be estimated, as well. It is thus impossible to determine a range for the breakdown conditions of the gas discharge tube, based on the irradiation conditions provided by the light source.

The light source for pre-energizing the gas discharge tube makes the breakdown conditions substantially independent from environmental influences, such as ambient light or temperature. Regardless of whether the gas discharge tube is exposed to ambient light or not, the light source ensures minimal breakdown conditions at which the gas discharge tube will arc over in any event.

It would be also desirable that the light output produced by the light source is used in an efficient manner to pre-energize the gas discharge tube. This desire and/or possible other desires are addressed by the light source being situated in proximity to the gas discharge tube. The light source may also be oriented so that a direction of a maximum light density in a directional characteristic of the light source points to the gas discharge tube.

It would also be desirable if the gas discharge tube would be ready to arc over, i.e. changed from the high-impedance state to the short-circuit state, quickly at any time when a high-voltage pulse may occur. This desire and/or possible other desires are addressed by the light source being substantially permanently lit during an operation of the defibrillation circuit.

It would also be desirable if the defibrillation circuit or parts of the defibrillation circuit could be reliably protected against overvoltage. This desire and/or possible other desires are addressed by the gas discharge tube being arranged to function as an overvoltage protection device.

It would also be desirable for the light source to be energy-efficient, durable, and/or to produce minimal waste heat. At least one of these desires and/or possible other desires are addressed by the light source being in a form of a light emitting diode (LED).

It would be further desirable to protect voltage sensitive components of the defibrillation circuit. This desire and/or possible other desires are addressed by the defibrillation circuit further comprising an electrocardiogram monitoring circuit. The gas discharge tube is connected to the electrocardiogram monitoring circuit to function as an overvoltage protection device for the electrocardiogram monitoring circuit. The electrocardiogram monitoring circuit in the defibrillation circuit is usually voltage-sensitive due to the specifications that it has to meet, especially its ability to detect relatively weak voltages and currents.

The electrocardiogram monitoring circuit may comprise a plurality of monitoring leads, the defibrillation circuit may comprise an electrical conductor carrying an electrical reference potential sufficient to absorb excess electrical charge and the gas discharge tube may be connected between one of the monitoring leads and the electrical conductor carrying the electrical reference potential. Whenever the voltage between the monitoring lead and the electrical conductor carrying the electrical reference potential exceeds a breakdown voltage of the gas discharge tube, the gas discharge tube arcs over and thus substantially creates a short circuit between the monitoring lead and the electrical conductor. Excess electrical charge present in the monitoring lead is conducted via the gas discharge tube to the electrical conductor carrying the electrical reference potential. The overvoltage between the monitoring lead and the reference potential vanishes or is reduced to a harmless value.

The defibrillation circuit may further comprise a plurality of further gas discharge tubes connected between one of the further monitoring leads and the electrical conductor carrying the electrical reference potential. Thus, further monitoring leads or all monitoring leads are protected by an individual gas discharge tube. A high-voltage pulse may occur between two of the plurality of monitoring leads so that both gas discharge tubes might arc over in order to connect the two monitoring leads with each other via the electrical conductor carrying the electrical reference potential in a near-short-circuit manner.

The defibrillation circuit may further comprise a light-proof or an opaque housing for the gas discharge tube and the light source for providing predictable pre-energizing conditions for the gas discharge tube. The light-proof housing may be the housing of the defibrillation circuit itself, for example the housing of an AED.

In an alternative aspect of the teachings disclosed herein, it would be desirable to provide a means for overvoltage protection in medical devices that is reliable and exhibits substantially constant breakdown conditions. This desire and/or possible other desires are addressed by an overvoltage protection device for a medical device, the overvoltage protection device comprising a gas discharge tube and a light source arranged to pre-energize the gas discharged tube in order to provide predictable breakdown conditions of the gas discharge tube.

The light source for pre-energizing the gas discharge tube makes the breakdown conditions substantially independent from environmental influences, such as ambient light or temperature. Regardless of whether the gas discharge tube is exposed to ambient light or not, the light source ensures minimal breakdown conditions at which the gas discharge tube will arc over in any event.

The light source may be situated in proximity to the gas discharge tube.

The light source may be substantially permanently lit during the armed state (operational state) of the overvoltage protection device.

The light source may be a light emitting diode (LED).

In yet an alternative aspect of the teachings disclosed herein, it would be desirable to provide a method for overvoltage protection in medical devices that is reliable and exhibits substantially constant breakdown conditions. These desires and/or possible other desires are addressed by a method of using a gas discharge tube in a medical device, the method comprising:

lighting a light source situated in a proximity of the gas discharge tube, thereby pre-energizing the gas discharge tube to provide predictable breakdown conditions of the gas discharge tube;

having the gas discharge tube arc over in response to an overvoltage applied to the gas discharge tube, the overvoltage being beyond the predictable breakdown conditions.

These and other aspects of the invention will be apparent from and illustrated with reference to the embodiment(s) described herein after.

DETAILED DESCRIPTION OF THE EMBODIMENTS

The invention will now be described on the basis of the drawings. It will be understood that the embodiments and aspects of the invention described herein are only examples and do not limit the protective scope of the claims in any way. The invention is defined by the claims and their equivalence. It will also be understood that features of an aspect can be combined with a feature of a different aspect or aspects.

Figure 1:
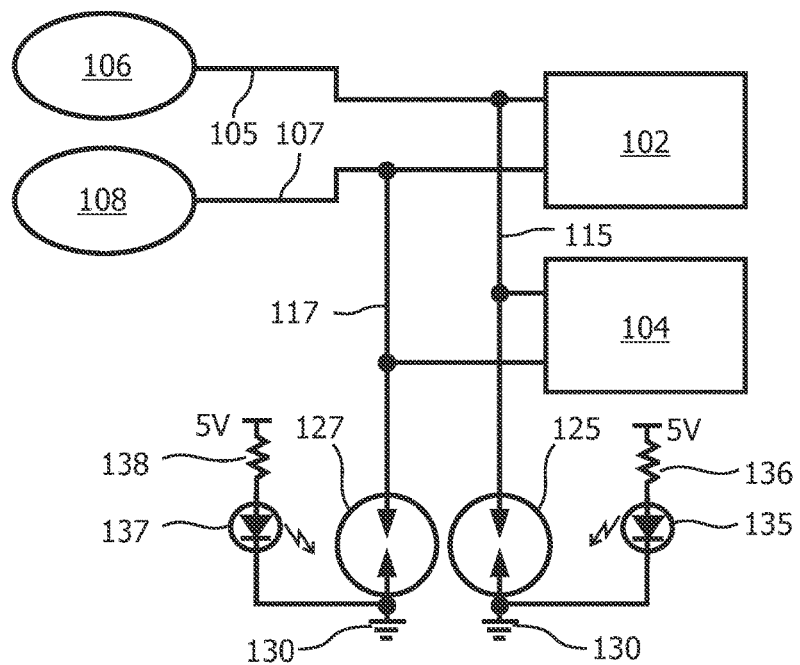
FIG. 1 shows a schematic block diagram of a first embodiment of a defibrillation circuit according to the teachings disclosed herein.

FIG. 1 shows in a schematic manner a block diagram of a defibrillation circuit according to the teachings disclosed herein. The defibrillation circuit comprises a high-voltage circuit 102 arranged to deliver a high-voltage pulse to a patient requiring defibrillation. The high-voltage circuit 102 is connected to defibrillation pads 106, 108 by means of two defibrillation leads 105, 107. The defibrillation pads 106, 108 may be adhesive pads that are attached to the patient prior to the beginning of a defibrillation procedure.

The defibrillation circuit further comprises an electrocardiogram (ECG) monitoring circuit 104. The ECG monitoring circuit 104 is indirectly connected to the defibrillation pads 106, 108 by means of two monitoring leads 115, 117, which are connected to the defibrillation leads 105 and 107 respectively. In this configuration of a defibrillator, only two electrode pads are needed because the defibrillation pads 106, 108 are also used for ECG monitoring. Having only two defibrillation pads 106, 108 facilitates a quick placement of the defibrillation pads 106, 108 especially in case the defibrillator is used by a lay person.

Whenever the high-voltage circuit 102 applies a high-voltage pulse to the defibrillation pads 106, 108 the ECG monitoring circuit 104 receives the high-voltage pulse (or a significant part thereof) because of the direct galvanic connection between the high-voltage circuit 102 and the ECG monitoring circuit 104. While the ECG monitoring circuit 104 may be designed to withstand normal high-voltage pulses by the high-voltage circuit 102, it is possible that the ECG monitoring circuit 104 receives overvoltage pulses. For example, one of the defibrillation pads 106, 108 might not be properly attached to the patient so that no current or only a small current can flow via the interface between the defibrillation pad and the skin of the patient. As a consequence, the high-voltage pulse tends to be discharged via another conducting path than the patient. This other conducting path may comprise the ECG monitoring circuit 104. The ECG monitoring circuit 104 comprises terminals that are used for connecting the monitoring leads 115, 117 with the ECG monitoring circuit 104. In order to avoid that the charge of the high-voltage pulse is discharged via the ECG monitoring circuit 104, the terminals of the ECG monitoring circuit are also connected to overvoltage protection devices, respectively. A first overvoltage protection device comprises a gas discharge tube 125 which is connected to the ECG monitoring lead 115 at a first terminal of the gas discharge tube 125. The gas discharge tube 125 is also connected to an electrical ground potential 130 at another terminal of the gas discharge tube 125. A light emitting diode (LED) 135 is located in a proximity to the gas discharge tube 125. A resistor 136 is connected in series with the light emitting diode 135 and also to a 5 volt electrical potential (5V). The light emitting diode 135 is also connected to the electrical reference potential 130. The series resistor 136 limits a current flowing through the light emitting diode 135 to a value that is suited for a long-term operation of the light emitting diode 135 and yields a sufficient light output of the LED 135.

The light output produced by the light emitting diode 135 is directed in the direction of the gas discharge tube 125. The gas discharge tube 125 becomes pre-energized due to an ionizing effect of the light from the LED 135 on the gas contained in the gas discharge tube 125. Another effect that may become relevant is the photoelectric effect by which electrons may be liberated in the anode or the cathode of the gas discharge tube 125.

The ECG monitoring lead 117 is also connected to a gas discharge tube 127 which is, in turn, connected to the electrical reference potential 130. A light emitting diode 137 (LED) is located in a proximity of the gas discharge tube 127. A series resistor 138 limits a current flowing through the light emitting diode 137. The series resistor 138 is also connected to a 5 volt electrical potential 5V, which could be the same as described previously in connection with the light emitting diode 135 and the series resistor 136. Instead of 5V another electrical potential adapted to operate a light emitting diode could be used, such as 3V.

The emitting diode 135, 137 could also be connected to some control circuitry in order to switch the light emitting diode 135, 137 on and off as required. It is also possible to use a variable resistor in addition to the series resistors 136 or 138, or as a replacement for the resistor 136 or 138. The variable resistor could be used to change the current flowing through the light emitting diode 135 or 137, thus adjusting the light output of the light emitting diode. In turn, the break down conditions of the gas discharge tube 125 or 127 could be adjusted within a certain range.

Figure 2:
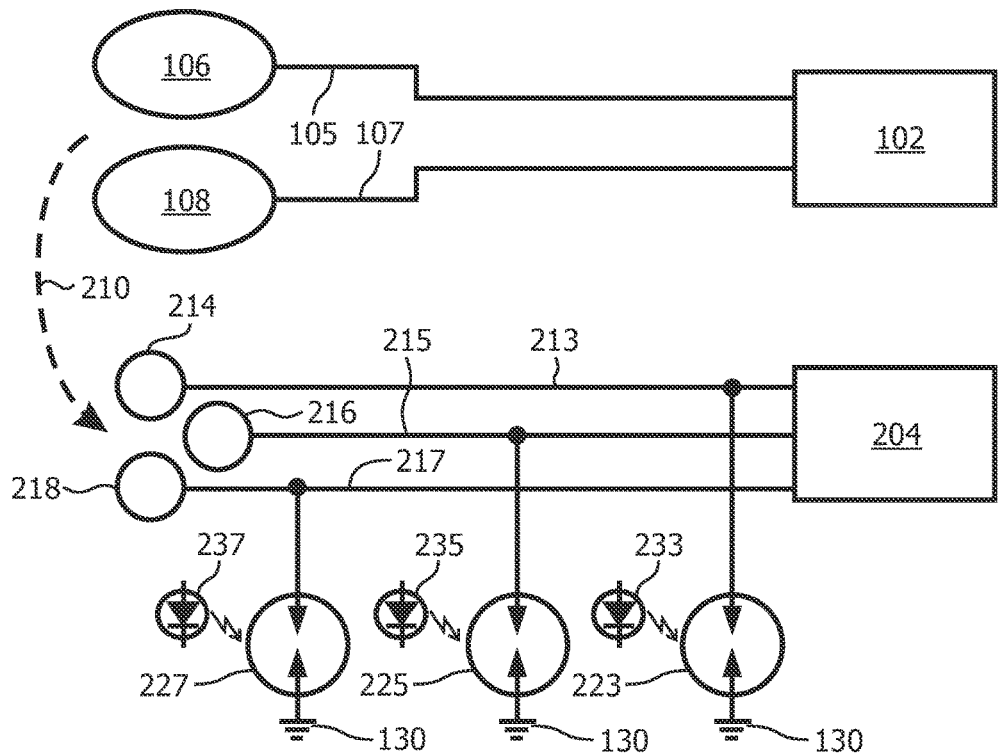
FIG. 2 shows a schematic block diagram of another embodiment of the defibrillation circuit according to the teachings disclosed herein.

FIG. 2 shows in a schematic manner a block diagram of a defibrillation circuit according to another embodiment of the teachings disclosed herein.

The high-voltage part is basically unchanged compared to FIG. 1. The high-voltage part comprises the high-voltage circuit 102, the defibrillation leads 105, 107 and the defibrillation pads 106, 108.

The ECG monitoring part of the defibrillation circuit shown in FIG. 2 is separate from the high-voltage part. The ECG monitoring pads comprises three ECG monitoring pads 214, 216, 218 (could be only two ECG monitoring pads or more than three ECG monitoring pads). The first ECG monitoring pad 214 is connected to an ECG monitoring lead 213 for connection to the ECG monitoring circuit 204. The second ECG monitoring pad 216 is connected to a second ECG monitoring lead 215 for connecting to the ECG monitoring circuit 204 and the third ECG monitoring pad 218 is connected to a third ECG monitoring lead 217 for connection to the ECG monitoring circuit 204.

During an operation of the defibrillation circuit, a coupling 210 occurs between the defibrillation pads 106, 108 and the ECG monitoring pads 214, 216, 218. In order to avoid damage to the ECG monitoring circuit 204, the ECG monitoring leads 213, 215, 217 are overvoltage protected by means of individual gas discharge tubes 223, 225, 227, connected to the reference potential 130.

As in FIG. 1, pre-energizing the gas discharge tubes 223, 225, 227 is achieved by light emitting diodes 233, 235, 237. For the sake of clarity, the supply circuitry for the various light emitting diodes 233, 235, 237 is not illustrated in FIG. 2.

In comparison to the gas discharge tubes 125, 127 of the embodiment shown in FIG. 1, the gas discharge tube 223, 225, 227 in FIG. 2 may be chosen to have a lower break down voltage and thus to more efficiently protect the ECG monitoring circuit 204. The reason is that there is no direct galvanic coupling between the high-voltage part and the ECG monitoring part of the defibrillation circuit. Shorting the ECG monitoring leads 213, 215, 217 to the reference potential 130 in response to a high-voltage pulse administered by the high-voltage circuit 102 does not have a large influence on the high-voltage pulse experienced by the patient.

Figure 3:
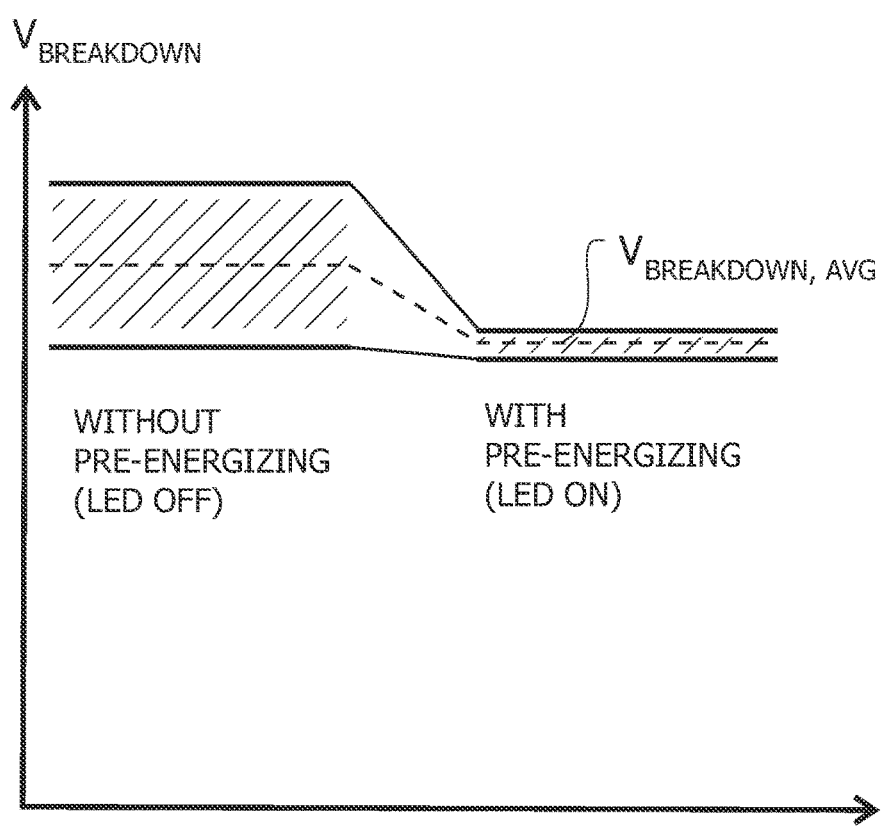
FIG. 3 shows a chart illustrating the effect of the teachings disclosed herein.

FIG. 3 shows a schematic diagram of an effect of pre-energizing the gas discharge tube 127 with light. To the left, the range of the break down voltage $V_{BREAKDOWN}$ can be seen for the case in which the gas discharge tube is not pre-energized. The break down voltage $V_{BREAKDOWN}$ is relatively high and may assume any value within a relatively large range of possible breakdown voltages. This is especially true for a first arcing-over event of the gas discharge tube 127 after some time of inactivity. The reason is that only a few gas molecules inside the gas discharge tube 127 are energized for the purposes of overvoltage protection. Without adequate pre-energization it cannot be relied upon the gas discharge tube arcing over at a certain desired voltage.

On the right side of FIG. 3 the situation is depicted when the gas discharge tube 127 is pre-energized, i.e. the light emitting diode is switched on and illuminates the gas discharge tube 127. The average break down voltage $V_{BREAKDOWN,AVG}$ is slightly lower compared to the non-pre-energized situation as illustrated on the left of FIG. 3. Perhaps even more important may be that the range of incertitude of the exact value of the break down voltage is now smaller. Thus, it can be expected that, in the pre-energized state shown on the right side of FIG. 3, the gas discharge tube arcs over when a voltage is applied to the gas discharge tube that is between the upper limit of the indicated range and the lower limit of the indicated range, at least under normal circumstances.

Other variations to the disclosed embodiment can be understood and effected by those skilled in the art in practicing the claimed invention from a study of the drawings, the disclosure, and the appended claims. In the claims, the word "comprising" does not exclude other elements or steps and the indefinite article "a" or "an" does not exclude a plurality. A single unit may perform functions of several items recited in the claims and vice versa. The mere fact that certain measures are resulted in mutually different dependent claims does not mean the combinations of these measures cannot be used to advantage. Any reference signs found in the claims should not be construed as limiting the scope.

The invention claimed is:

1. A defibrillation circuit comprising:
an electrode pad disposed to be adhesively attached to a patient; a defibrillation high-voltage circuit electrically connected to the electrode pad with a defibrillation lead; an electrocardiogram (ECG) monitoring circuit electrically connected to the electrode pad with a monitoring lead;
a gas discharge tube electrically connected to both of the defibrillation lead and the monitoring lead at a first terminal and to an electrical ground potential at a second terminal, wherein the gas discharge tube is arranged to function as an overvoltage protection device in the event that the electrode pad is not properly attached to the patient during a defibrillation pulse, wherein an overvoltage condition at the first terminal causes the gas discharge tube to discharge both the defibrillation lead and the electrocardiogram monitoring lead so as to protect the electrocardiogram monitoring circuit from the overvoltage condition;
a light source arranged to pre-energize the gas discharge tube in order to provide predictable breakdown conditions of the gas discharge tube; and
a source of current to the light source sufficient to illuminate the gas discharge tube such that a range of incertitude of the value of the gas discharge tube break down voltage is smaller.

2. The defibrillation circuit according to claim 1, wherein the light source is situated in proximity to the gas discharge tube.

3. The defibrillation circuit according to claim 1, wherein the light source is substantially permanently lit during an operation of the defibrillation circuit.

4. The defibrillation circuit according to claim 1, wherein the light source is a light emitting diode.

5. The defibrillation circuit according to claim 1, further comprising a light-proof housing for the gas discharge tube and the light source for providing predictable pre-energizing conditions for the gas discharge tube.

6. The defibrillation circuit of claim 1, further comprising:
a second electrode pad disposed to be adhesively attached to the patient, wherein the second electrode pad is electrically connected to both of the defibrillation high-voltage circuit with a second defibrillation lead and to the electrocardiogram (ECG) monitoring circuit with a second monitoring lead;
a second gas discharge tube electrically connected to both of the second defibrillation lead and the second monitoring lead at a third terminal and to an electrical ground potential at a fourth terminal, wherein the second gas discharge tube and the gas discharge tube are arranged to function as the overvoltage protection device;
a second light source arranged to pre-energize the second gas discharge tube in order to provide predictable breakdown conditions of the second gas discharge tube; and
a second source of current to the second light source sufficient to illuminate the second gas discharge tube such that a second range of incertitude of the value of the second gas discharge tube break down voltage is smaller.

* * * * *